United States Patent [19]

Tobert

[11] 4,217,340
[45] Aug. 12, 1980

[54] RAPID ACTING COMBINATION OF PHENYL BENZOIC ACID COMPOUNDS AND MAGNESIUM HYDROXIDE

[75] Inventor: Jonathan A. Tobert, Plainsboro, N.J.

[73] Assignee: Merck & Co., Inc., Rahway, N.J.

[21] Appl. No.: 22,384

[22] Filed: Mar. 21, 1979

[51] Int. Cl.² .................. A61K 31/60; A61K 31/605; A61K 33/08

[52] U.S. Cl. .................................... 424/157; 424/230; 424/235

[58] Field of Search ........................ 424/230, 235, 157

[56] References Cited

U.S. PATENT DOCUMENTS

| 3,674,870 | 7/1972 | Ruyle et al. ........................... 424/230 |
| 3,689,644 | 9/1972 | Plotnikoff ............................. 424/157 |
| 3,714,226 | 1/1973 | Ruyle et al. ........................ 260/473 S |

OTHER PUBLICATIONS

Chem. Abst. 87-161544S (1977).
Garnham et al., *Postgraduate Medical Journal*, 53, 126-129 (Mar. 1977).
Ambre and Fischer, *Clinical Pharmacology and Therapeutics*, vol. 14, No. 2, pp. 231-237 (1972).

*Primary Examiner*—Stanley J. Friedman
*Attorney, Agent, or Firm*—Raymond M. Speer; Mario A. Monaco

[57] ABSTRACT

A novel, rapid acting drug combination comprising a phenyl benzoic acid compound and magnesium hydroxide. The combination results in earlier, higher plasma levels of the analgesic, anti-inflammatory drug.

8 Claims, No Drawings

RAPID ACTING COMBINATION OF PHENYL BENZOIC ACID COMPOUNDS AND MAGNESIUM HYDROXIDE

BACKGROUND OF THE INVENTION

1. Field of the Invention

The present invention relates to a novel drug combination for more effective treatment of pain and inflammation.

Particularly, the present invention is concerned with the combination of an analgesic, anti-inflammatory phenyl benzoic acid compound and magnesium hydroxide.

2. Brief Description of the Prior Art

The phenyl benzoic acid compounds employed in the present invention are known analgesic and anti-inflammatory compounds. See U.S. Pat. Nos. 3,674,870 and 3,714,226.

The interaction of various antacids and various drugs, including non-steroidal anti-inflammatory drugs, has never been predictable with any acceptable degree of accuracy. See, for example, Garnham et al., *Postgraduate Medical Journal*, 53, 126–129 (March 1977), which discusses the different effects of sodium bicarbonate and aluminum hydroxide on the adsorption of indomethacin in man, as well as other drug/antacid interactions, and some theories of action concerning these. See also Ambre and Fischer, *Clinical Pharmacology and Therapeutics*, Vol. 14, No. 2, pp. 231–237 (1972), which discloses increased absorption of bishydroxycoumarin when administered with magnesium hydroxide.

SUMMARY OF THE INVENTION

In accordance with the present invention there is provided a novel, rapid acting drug combination for more effective treatment of pain and inflammation comprising (a) from 5 to 60% by weight of a phenyl benzoic acid compound, and (b) from 95 to 40% by weight of magnesium hydroxide. Preferably, from 20 to 30% by weight of the phenyl benzoic acid compound, and from 80 to 70% by weight of the magnesium hydroxide are employed.

The phenyl benzoic acid compounds which comprise the active analgesic, anti-inflammatory ingredient of the novel drug combination of the present invention are selected from compounds of the general formula:

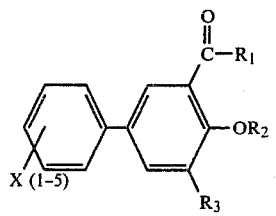

(I)

wherein X (1–5) is halo, such as fluoro or chloro, but especially fluoro; X being on one or more of the phenyl carbon atoms;

$R_1$ is selected from the grop consisting of hydroxy, phenoxy diloweralkylamino (such as dimethylamine), diloweralkylamino loweralkoxy (such as diethylaminoethoxy);

$R_2$ is selected from the group consisting of hydrogen and lower alkanoyl (such as acetyl, propionyl and butyryl); and $R_3$ is selected from the group consisting of hydrogen and methyl.

Also included are the pharmaceutically non-toxic salts of the acids of the compounds of Formula I such as the ammonium, alkali metal (such as sodium or potassium); alkaline earth metals (such as calcium, barium, or magnesium); amine; aluminum; iron; choline; glucosamine; S-methyl methonine salts, piperazine, diloweralkylamino lower alkanol, chloroquine and hydroxy chloroquine; the anhydride of said acids, the mixed anhydrides of said acids and 2-acetoxy benzoic acid.

Especially preferred phenyl benzoic acid compounds are those wherein;

$R_1$ is hydroxy,
$R_2$ is hydrogen or acetyl,
$R_3$ is hydrogen, and
X is fluoro, X being on any position of the phenyl moiety when X is one fluoro group, but particularly on the 4'-position; and where X represents two fluoro groups, particularly on the 2'- and 4'-positions.

Representative phenyl benzoic acid compounds are as follows:

2-hydroxy-5-(2',4'-difluorophenyl)benzoic acid;
2-acetoxy-5-(2',4'-difluorophenyl)benzoic acid;
2-hydroxy-5-(2'-fluorophenyl)benzoic acid;
2-hydroxy-5-(4'-fluorophenyl)benzoic acid;
2-hydroxy-5-(3'-fluorophenyl)benzoic acid;
2-hydroxy-5-pentafluorophenyl benzoic acid;
2-hydroxy-3-methyl-5-(2',4'-difluorophenyl)benzoic acid;
2-hydroxy-5-(2'-chloro-4'-fluorophenyl)benzoic acid;
N,N-dimethyl-5-(2',4'-difluorophenyl)salicylamide;
β-diethylaminoethyl-4-(2',4'-difluorophenyl)salicylate;
phenyl-5-(2',4'-difluorophenyl)salicylate;
aluminum-2-acetoxy-5-(2',4'-difluorophenyl)-benzoate salt;
aluminum-2-hydroxy-5-(2',4'-difluorophenyl)-benzoate salt;
choline-2-acetoxy-5-(2',4'-difluorophenyl)-benzoate salt;
choline-2-hydroxy-5-(2',4'-difluorophenyl)-benzoate salt;
sodium-2-acetoxy-5-(2',4'-difluorophenyl)-benzoate salt;
sodium-2-hydroxy-5-(2',4'-difluorophenyl)-benzoate salt;
2-acetoxy-5-(pentafluorophenyl)-benzoic acid;
β-diethylaminoethyl-2-hydroxy-5-(2',4'-difluorophenyl)benzoate;
β-diethylaminoethyl-2-acetoxy-5-(2',4'-difluorophenyl)benzoate.

An especially preferred phenyl benzoic acid compound for use in the present invention is 2-hydroxy-5-(2',4'-difluorophenyl) benzoic acid, which, for convenience, may be identified by its shorter generic name: diflunisal.

The present invention is concerned broadly with a method of treating pain and inflammation comprising coadministering to a patient in need of such treatment a therapeutically effective amount of a phenyl benzoic acid compound as utilized in the present invention, and magnesium hydroxide. Such co-administration may simply take the form of simultaneous, or at least concurrent, administration of the phenyl benzoic acid compound and magnesium hydroxide, without any requirement that the two compounds be physically combined.

More advantageously, however, co-administration will take the form of treatment utilizing a physical mixture of the phenyl benzoic acid compound and magnesium hydroxide together with a pharmaceutically acceptable carrier.

The treatment of pain and inflammation is in accordance with the preferred method of the present invention is accomplished by orally administering to patients in need of such treatment a composition having as its active ingredient a mixture of from 5 to 60% by weight of a compound of Formula I, particularly the especially preferred compounds, and from 95 to 40% by weight of magnesium hydroxide, in a non-toxic pharmaceutically acceptable carrier, preferably in tablet or capsule form.

The non-toxic pharmaceutical carrier may be for example, either a solid or a liquid. Exemplary of solid carriers are lactose, corn starch, gelatin, talc, stearic acid, magnesium stearate, terra alba, sucrose, agar, pectin, cab-o-sil, and acacia. Exemplary of liquid carriers are peanut oil, olive oil, sesame oil and water. Similarly, the carrier or diluent may include a time delay material such as glyceryl monostearate or glyceryl distearate alone or with a wax.

Several pharmaceutical forms of the therapeutically useful compositions can be used. For example, if a solid carrier is used, the compositions may take the form of tablets, capsules, powders, troches or lozenges, prepared by standard pharmaceutical techniques. If a liquid carrier is used, the preparation may be in the form of a syrup or a liquid suspension.

The active compounds of Formula I and the compositions of this invention are present in an amount sufficient to treat pain and inflammation, that is, to reduce pain and inflammation. Advantageously, the composition will contain the active ingredient, namely, the compounds of Formula I in an amount of from about 1 mg. to 140 mg. per kg. body weight per day (50 mg. to 10 g. per patient per day), preferably from about 2 mg. to 70 mg. per kg. body weight per day (100 mg. to 5 g. per patient per day).

The magnesium hydroxide component of the novel drug combination of the present invention is present in an amount sufficient to obtain rapid action improved effectiveness in the form of higher plasma levels of the phenyl benzoic acid compound active ingredient during the first 1 to 2 hours after administration, as described in detail hereinafter. A sufficient amount of magnesium hydroxide for this purpose is present when from 95 to 40% by weight of the magnesium hydroxide is employed, based on the total weight of magnesium hydroxide and compound of Formula I, as described above.

The preferred method of treatment of this invention comprises internally administering to a patient (animal or human), compounds of Formula I and magnesium hydroxide, particularly including an especially preferred compound of Formula I, admixed with a non-toxic pharmaceutical carrier such as exemplified above. The mixture of the compound of Formula I and magnesium hydroxide will be present in an amount of from 1 mg. to 140 mg./kg. body weight per day, preferably from about 2 mg. to about 70 mg. per kilogram body weight per day and especially from 4 mg. to 10 mg./kg. body weight per day. The most rapid and effective analgesic and anti-inflammatory effect is obtained from oral administration of a daily dosage of from about 4 to 10 mg./kg. per day. It should be understood, however, that although preferred dosage ranges are given, the dose level for any particular patient depends upon the activity of the specific compound empolyed. Also many other factors that modify the actions of drugs will be taken into account by those skilled in the art in the therapeutic use of medicinal agents, particularly those of Formula I, for example, age, body, weight, sex, time of administration, route of administration, rate of excretion, drug combination, reaction sensitivities and severity of the particular disease.

It is generally accepted that the more rapidly a drug is absorbed, the earlier its onset of action will occur. The more rapid absorption can be demonstrated by measuring the plasma levels of the drug. Accordingly, the novel drug combination of the present invention was evaluated in an open, randomized and balanced, single dose study in twelve healthy male subjects. Subjects were between the ages of 18 an 45 years of age and weighed within ±15% of their ideal body weight for their ages and heights. All subjects were judged to be in good health on the basis of history, physical examination, and routine laboratory data. Each subject received the following treatments at intervals of at least five days:

Treatment 1—Fasted/control: 250 mg. of diflunisal alone in the fasting state.

Treatment 2—Fasted/Mg(OH)$_2$: 250 mg. of diflunisal plus 10 ml. of magnesium hydroxide mixure (800 mg.) in the fasting state.

The diflunisal was taken as a single oral dose with two full glasses of water (400 ml.). In Treatment 2, the magnesium hydroxide was taken first, followed immediately by the dose of diflunisal. No other drugs, including headache and cold remedies, were taken after seven days prior to, or during the study.

The plasma levels were determined after a single dose. Five ml. of venous blood were drawn into heparinized tubes at the following times, where 0 hours represents the time of drug administration: −0.25 to 0, 0.5, 1, 2, 3, 4, 6, and 8. The blood was centrifuged immediately and the plasma was separated. The diflunisal determination was done using the fluorescense method described by Tocco, D. J. et al., *Drug Metabolism and Disposition*, 3: 453–466 (1975), with minor changes in procedure as described below. The plasma samples were acidified with perchloric acid and extracted with chloroform. The chloroform solution was then extracted with a pH 8 phosphate buffer and the fluorescence in the aqueous phase measured in a spectrophotofluorometer set at 305 nm (activation) and 425 nm (emission) wave lengths. The fluorescence was proportional to the absolute amount of diflunisal over the range of 0.5 to 30 μg. When known amounts of diflunisal were added to plasma, 84±3% was recovered.

The results of the evaluation are set out in the following table of data:

TABLE

| SUBJECT NUMBER | Time (Hours following dose) | | | | | | | |
|---|---|---|---|---|---|---|---|---|
| | 0 | 0.5 | 1 | 2 | 3 | 4 | 6 | 8 |
| DIFLUNISAL PLASMA CONCENTRATION (μg/ml) FOLLOWING TREATMENT 1 (FASTED/CONTROL) | | | | | | | | |
| 1 | 0 | 0.6 | 4.2 | 30.5 | 24.8 | 18.7 | 18.7 | 15.6 |
| 2 | 0 | 8.2 | 6.9 | 16.0 | 21.6 | 38.0 | 27.2 | 22.8 |
| 3 | 0 | 9.7 | 21.0 | 24.1 | 32.4 | 28.0 | 21.6 | 17.0 |
| 4 | 0 | 3.0 | 7.8 | 35.5 | 30.3 | 25.0 | 21.2 | 18.4 |
| 5 | 0 | 3.8 | 7.4 | 26.0 | 30.6 | 26.4 | 21.4 | 19.8 |
| 6 | 0 | 2.7 | 16.2 | 24.0 | 24.7 | 19.0 | 13.4 | 12.0 |
| 7 | 0 | 27.0 | 41.9 | 32.8 | 27.3 | 24.4 | 19.7 | 17.0 |
| 8 | 0 | 4.2 | 35.6 | 36.0 | 28.4 | 24.8 | 22.0 | 17.4 |

TABLE-continued

| SUBJECT NUMBER | Time (Hours following dose) | | | | | | |
|---|---|---|---|---|---|---|---|
| | 0 | 0.5 | 1 | 2 | 3 | 4 | 6 | 8 |
| 9 | 0 | 2.0 | 11.0 | 45.0 | 35.8 | 27.0 | 20.4 | 15.4 |
| 10 | 0 | 0 | 3.4 | 11.7 | 41.4 | 33.1 | 24.7 | 20.6 |
| 11 | 0 | 10.6 | 33.2 | 40.9 | 36.8 | 33.9 | 29.2 | 20.0 |
| 12 | 0 | 19.3 | 35.4 | 33.6 | 27.2 | 23.7 | 19.2 | 15.1 |
| MEAN | — | 7.5 | 18.7 | 29.7 | 30.5 | 27.3 | 21.5 | 17.6 |

DIFLUNISAL PLASMA CONCENTRATION (μg/ml) FOLLOWING TREATMENT 2 (FASTED/Mg(OH)₂)

| 1 | 0 | 22.6 | 40.2 | 33.0 | 27.7 | 23.6 | 19.2 | 16.9 |
| 2 | 0 | 0.4 | 4.4 | 15.6 | 32.6 | 37.8 | 26.6 | 22.0 |
| 3 | 0 | 7.6 | 18.1 | 40.0 | 35.6 | 28.1 | 21.6 | 17.8 |
| 4 | 0 | 3.8 | 20.8 | 35.6 | 30.1 | 24.0 | 19.3 | 16.6 |
| 5 | 0 | 4.6 | 17.8 | 18.7 | 20.4 | 22.6 | 21.1 | 17.6 |
| 6 | 0 | 29.4 | 33.4 | 27.5 | 23.7 | 20.2 | 15.1 | 11.7 |
| 7b | 0 | 22.3 | 41.9 | 34.0 | 28.3 | 24.5 | 19.0 | 15.4 |
| 8 | 0 | 37.2 | 38.5 | 38.1 | 30.7 | 30.0 | 22.3 | 18.4 |
| 9 | 0 | 1.8 | 21.7 | 36.8 | 30.4 | 26.0 | 20.5 | 17.2 |
| 10 | 0 | 2.0 | 35.6 | 39.0 | 32.6 | 27.6 | 22.4 | 18.9 |
| 11 | 0 | 35.7 | 55.6 | 55.2 | 44.3 | 38.8 | 28.4 | 24.9 |
| 12 | 0 | 42.4 | 39.7 | 35.8 | 29.9 | 23.7 | 20.6 | 16.2 |
| MEAN | — | 17.4 | 30.6 | 34.1 | 30.5 | 27.2 | 21.3 | 17.8 |

What is claimed is:

1. In combination:

(a) from 5 to 60% by weight of a phenyl benzoic acid compound of the general formula:

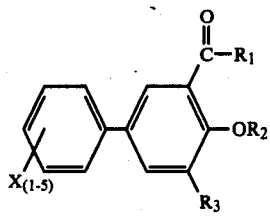

wherein $X_{(1-5)}$ is halo; X being on one or more of the phenyl carbon atoms;

$R_1$ is selected from the group consisting of hydroxy, phenoxy, diloweralkylamino, and diloweralkylamino loweralkoxy;

$R_2$ is selected from the group consisting of hydrogen and lower alkanoyl; and $R_3$ is selected from the group consisting of hydrogen and methyl;

and pharmaceutically acceptable, non-toxic salts thereof;

and (b) from 95 to 40% by weight of magnesium hydroxide.

2. The combination of claim 1 wherein the phenyl benzoic acid compound is 2-hydroxy-5-(2',4'-difluorophenyl)benzoic acid.

3. A method of treating pain and inflammation which comprises orally co-administering to a patient in need of such treatment, daily doses of from 1 mg. to 140 mg./kg. of body weight of (a) a phenyl benzoic acid compound of the general formula:

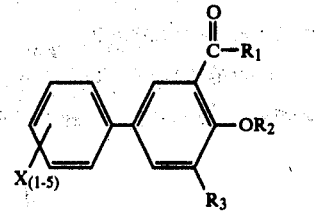

wherein $X_{(1-5)}$ is halo; X being on one or more of the phenyl carbon atoms;

$R_1$ is selected from the group consisting of hydroxy, phenoxy, diloweralkylamino, and diloweralkylamino loweralkoxy;

$R_2$ is selected from the group consisting of hydrogen and lower alkanoyl; and $R_3$ is selected from the group consisting of hydrogen and methyl;

and pharmaceutically acceptable, non-toxic salts thereof;

and (b) magnesium hydroxide;

wherein the total daily dose comprises from 5 to 60% by weight of (a) the phenyl benzoic acid compound, and from 95 to 40% by weight of (b) magnesium hydroxide.

4. The method of claim 3 wherein the phenyl benzoic acid compound is 2-hydroxy-5-(2',4'-difluorophenyl)benzoic acid.

5. A method of treating pain and inflammation which comprises orally administering to a patient in need of such treatment, daily doses of from 1 mg. to 140 mg./kg. of body weight of the combination of (a) from to % by weight of a phenyl benzoic acid compound of the general formula:

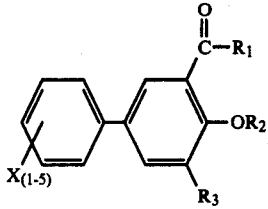

wherein $X_{(1-5)}$ is halo; X being on one or more of the phenyl carbon atoms;

$R_1$ is selected from the group consisting of hydroxy, phenoxy, diloweralkylamino, and diloweralkylamino loweralkoxy;

$R_2$ is selected from the group consisting of hydrogen and lower alkanoyl; and $R_3$ is selected from the group consisting of hydrogen and methyl;

and pharmaceutically acceptable, non-toxic salts thereof;

and (b) from 95 to 40% by weight of magnesium hydroxide.

6. The method of claim 5 wherein the phenyl benzoic acid compound is 2-hydroxy-5-(2',4'-difluorophenyl)benzoic acid.

7. A pharmaceutical composition for treating pain and inflammation comprising a unit dosage form for oral administration containing a therapeutically effective amount of the combination (a) from 5 to 60.0% by weight of a phenyl benzoic acid compound of the general formula:

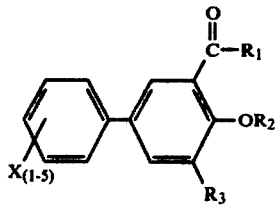

wherein $X_{(1-5)}$ is halo; X being on one or more of the phenyl carbon atoms;

$R_1$ is selected from the group consisting of hydroxy, phenoxy, diloweralkylamino, and diloweralkylamino loweralkoxy;

$R_2$ is selected from the group consisting of hydrogen and lower alkanoyl; and $R_3$ is selected from the group consisting of hydrogen and methyl;

and pharmaceutically acceptable, non-toxic salts thereof;

and (b) from 95 to 40% by weight of magnesium hydroxide as an active ingredient; together with a pharmaceutically acceptable non-toxic carrier.

8. The composition of claim 7 wherein the phenyl benzoic acid compound is 2-hydroxy-5-(2',4'-difluorophenyl)benzoic acid.

* * * * *